(12) United States Patent
Xie (10) Patent No.: US 8,135,474 B1
(45) Date of Patent: Mar. 13, 2012

(54) COCHLEAR IMPLANT FOR AN IMPLANTABLE COCHLEAR STIMULATION SYSTEM AND METHOD OF ASSEMBLY

(75) Inventor: Jian Xie, Stevenson Ranch, CA (US)

(73) Assignee: Advanced Bionics, LLC, Valencia, CA (US)

( * ) Notice: Subject to any disclaimer, the term of this patent is extended or adjusted under 35 U.S.C. 154(b) by 704 days.

(21) Appl. No.: 12/329,338

(22) Filed: Dec. 5, 2008

(51) Int. Cl.
*A61N 1/375* (2006.01)

(52) U.S. Cl. ............... 607/57; 607/36; 607/55

(58) Field of Classification Search ......... 607/35–37.55, 607/57, 116
See application file for complete search history.

(56) References Cited

U.S. PATENT DOCUMENTS

| | | | |
|---|---|---|---|
| 5,244,707 A | 9/1993 | Shores | |
| 5,304,419 A | 4/1994 | Shores | |
| 5,401,536 A | 3/1995 | Shores | |
| 5,591,379 A | 1/1997 | Shores | |
| 6,011,993 A | 1/2000 | Tziviskos et al. | |
| 6,051,017 A | 4/2000 | Loeb et al. | |
| 6,067,474 A | 5/2000 | Schulman et al. | |
| 6,411,854 B1 | 6/2002 | Tziviskos et al. | |
| 6,537,688 B2 | 3/2003 | Silvernail et al. | |
| 6,897,474 B2 | 5/2005 | Brown et al. | |
| 7,132,173 B2 | 11/2006 | Daulton | |
| 7,211,881 B2 | 5/2007 | McKinnell et al. | |
| 2006/0173259 A1 | 8/2006 | Flaherty et al. | |
| 2007/0123938 A1 | 5/2007 | Haller et al. | |
| 2008/0046021 A1 | 2/2008 | Greenberg et al. | |
| 2008/0065181 A1 | 3/2008 | Stevenson | |

FOREIGN PATENT DOCUMENTS

WO 2008/007839 A1 1/2008

OTHER PUBLICATIONS

Ken Gilleo and Steve Corbett, Getters—Molecular Scavengers for Packaging, http://www.cooksonsemi.com/products/product. asp?ID=HiCap2000, www.hdi-online.com, Jan. 2001, pp. 26-29.
Ken Gilleo, MEMS Packaging Issues and Materials, http://www. cooksonsemi.com/products/product.asp?ID=HiCap2000.
Cookson Electronics, Technical Bulletin, HiCap 2000 High capacity moisture and CO2 getter, http://www.cooksonsemi.com/products/ polymer/technicalbulletins.asp.
Cookson Electronic Polymers Selector Guide, http://www. cooksonsemi.com/products/product.asp?ID=HiCap2000, Apr. 2007.
Hal Greenhouse, "Hermeticity of Electronic Packages," Noyes Publications, 2000, pp. 135-139.
James Cavuoto, "Neural engineering's image problem," Spectrum, IEEE, vol. 41, Issue 4, Apr. 2004, pp. 32-37.
Neyer, et al., "Aerospace Leak Test Requirements," Proceedings of 36th Joint Propulsion Conference, AIAA, Huntsville AL, Jul. 2000.

*Primary Examiner* — Carl H Layno
*Assistant Examiner* — Paula J Stice
(74) *Attorney, Agent, or Firm* — Mary Elizabeth Bush (57) ABSTRACT

A cochlear implant for a cochlear stimulation system and method of assembling the implant comprising an implantable sealed housing comprising a metal feedthrough case and a metal bottom cover and containing cochlea stimulation circuitry, the feedthrough case comprising silicone enclosed feedthrough pins for connecting an electrical lead of a cochlear electrode to the stimulation circuitry, and a moisture absorbing material comprising calcium oxide secured within the housing and sufficient in quantity to absorb moisture released by the circuitry materials and leaking into the feedthrough case at leak rates of about $1 \times 10^{-7}$ atm cc/s to maintain the cochlear implant within acceptable internal moisture limits for at least about 60 years.

30 Claims, 5 Drawing Sheets

COCHLEAR IMPLANT FOR AN IMPLANTABLE COCHLEAR STIMULATION SYSTEM AND METHOD OF ASSEMBLY

FIELD OF INVENTION

The present invention relates to cochlear stimulation systems and, more particularly, to an improved cochlear implant with a cured moisture absorbing material secured within its sealed and silicone enclosed metal housing. The cured moisture absorbing material comprises calcium oxide sufficient in quantity to absorb moisture leaking into the housing at leak rates of about $1\times10^{-7}$ atm cc/s or less where the cochlear implant meets or exceeds its operational moisture specifications for an extended period of time.

BACKGROUND OF INVENTION

Cochlear stimulation systems commonly comprise a cochlear implant, which includes an implantable sealed metal housing containing stimulation circuitry connected by metal feedthrough pins to an implantable cochlear electrode. While failures in such systems are relatively rare, when they occur they are often traced to the stimulation circuitry contained within the sealed metal housing. Such failures require a surgical removal and replacement of the cochlear implant.

After such removal, the sealed metal housing is opened and the stimulation circuitry examined to locate the failure and to determine the mechanism that caused the failure. One such failure mechanism is corrosion of or other damage to stimulation circuit components due the collection of ion-containing moisture within the sealed metal housing. Such moisture may be released by the circuitry materials and/or moisture that has leaked into the housing. One avenue for such moisture leakage into the housing has been found to be the insulating seals for the metal feedthrough pins connecting the stimulation circuitry to the cochlear electrode. Glass seals are commonly employed to hermetically seal and insulate the feedthrough pins in the metal housing. They have been found to be subject to cracking around the feedthrough pins when subjected to excessive forces during assembly, testing, or use of the stimulation circuitry.

Whatever the moisture source, it is important that it be eliminated or controlled so that ion-carrying moisture does not collect within the sealed metal housing of a cochlear implant in sufficient quantities as to produce an operational failure within its associated cochlear stimulation system. After extensive research and development, applicant and his associates have developed a system and method of assembly for controlling the collection of moisture within the metal housing of cochlear stimulation systems that will extend the potential reliable operational life of cochlear implants to more than 60 years.

SUMMARY OF INVENTION

Basically, the present invention is directed to a cochlear implant including an implantable sealed housing comprising a metal feedthrough case having metal top and bottom covers. The feedthrough case contains cochlea stimulation circuitry in a bottom compartment that is closed by the bottom cover, and includes metal feedthrough pins having lower ends electrically connected to the stimulation circuitry and extending upward from the bottom compartment through insulating seals into a top compartment of the feedthrough case bounded by the top cover, where upper ends of the feedthrough pins are electrically connected to an electrical lead from an implantable cochlear electrode completing connection of the cochlear electrode to the stimulation circuitry. The upper ends of the feedthrough pins and insulating seals are enclosed in a protective biocompatible material such as silicone rubber to limit the flow of moisture into the bottom compartment housing the stimulation circuitry as through any leak paths in the insulating seals or around the metal feedthrough pins to leak rates of up to about $1\times10^{-7}$ atm cc/s. In addition, the feedthrough case preferably is overmolded with silicone to insure that any moisture from any other source leaking into the bottom compartment of the feedthrough enters the bottom compartment at moisture leak rates less than about $1\times10^{-7}$ atm cc/s.

The free internal volume of the bottom compartment of the feedthrough case remaining after enclosing the components of the stimulation circuitry and the lower ends of the feedthrough pins is about 1.1 cc. Secured within that free volume is a quantity of a cured moisture absorbing material comprising calcium oxide sufficient in quantity to absorb moisture released by the stimulation circuitry and moisture leaking into the bottom compartment of the feedthrough case through any leak paths in the insulating seals or around the metal feedthrough pins or otherwise at leak rates up to about $1\times10^{-7}$ atm cc/s. At such moisture leak rates, about 30 mg or more of a cured moisture absorbing material containing calcium oxide has been found sufficient to absorb the released and leaking moisture and to protect and reliably extend the operational life of the associated cochlear stimulation circuitry to at least 60 years.

The foregoing as well as other structures, features, and methods of assembly of the present invention may be more fully understood by reference to the following detailed description referring to the drawings briefly described as follows.

DETAILED DESCRIPTION OF INVENTION

Basically, the present invention comprises a cochlear implant for a cochlear stimulation system and method of assembling the implant comprising an implantable sealed housing containing cochlear stimulation circuitry and a moisture absorbing material comprising calcium oxide secured within the housing and sufficient in quantity to absorb moisture released by materials comprising the stimulation circuitry and moisture leaking into the housing at a leak rate up to about $1 \times 10^{-7}$ atm cc/s. Uncured, the weight of the moisture absorbing material is preferably between about 60 mg and about 100 mg and after curing is preferably between about 30 mg and about 50 mg, and more preferably about 40 mg. The housing itself preferably comprises a silicone enclosed metal feedthrough case having top and bottom compartments respectively enclosed by top and bottom covers and having silicone enclosed metal feedthrough pins and insulating seals extending between the top and bottom compartments for connecting an electrical lead from a cochlear electrode to stimulation circuitry mounted in the bottom compartment of the feedthrough case.

As to the leaking of moisture into the sealed housing of the cochlear implant, it is recognized that there is a transition from mainly molecular moisture flow to mainly viscous moisture flow that occurs at leak rates of about $1 \times 10^{-5}$ atm cc/s. At leak rates above $1 \times 10^{-5}$ atm cc/s where the flow is viscous, a leaking sealed case will rapidly fill with liquid. At leak rates less than $1 \times 10^{-5}$ atm cc/s where the flow is molecular, a leaking sealed metal case will slowly fill with moisture. In his development of a system for extending the operating life of cochlear implants, applicant found and confirmed that there is a linear relationship between the useful life of sealed cochlear implants and moisture leak rates less than $1 \times 10^{-5}$ atm cc/s and that enclosing a feedthrough case and more particularly the metal feedthrough pins and insulating seals of such devices in silicone reduced the moisture leak rate into the case to about $1 \times 10^{-7}$ atm cc/s or less where applicant found that the inclusion of a moisture absorbing material or getter comprising cured calcium oxide in quantities of about 30 mg or more extended the useful life of the implanted device to 60 or more years.

Figure 1:
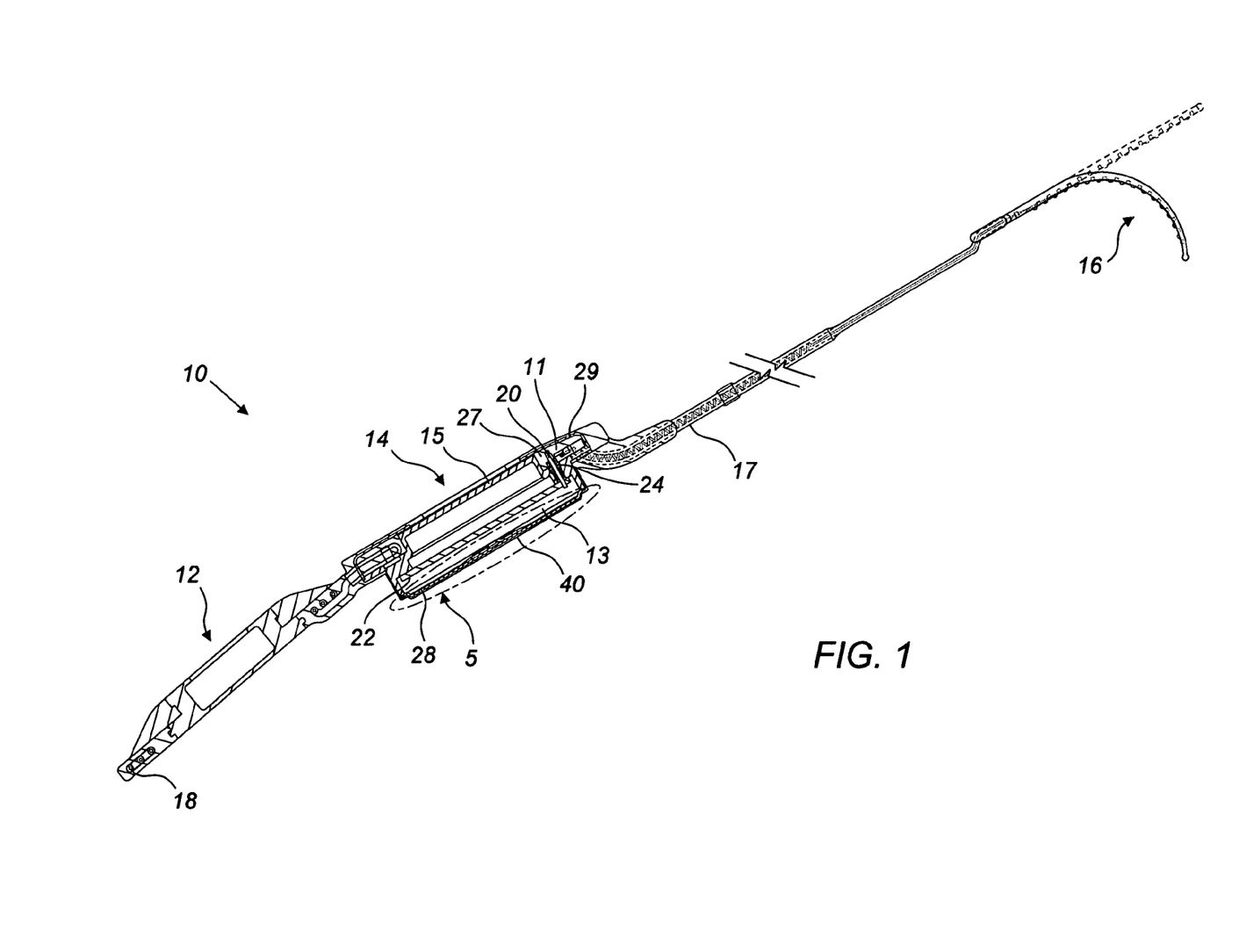
FIG. 1 is a sectional side view of a cochlear implant system comprising an antenna coil case, a cochlear electrode and a sealed housing comprising a metal feedthrough case sealed by metal top and bottom covers and containing cochlea stimulation circuitry connected by silicone enclosed metal feedthrough pins to the cochlear electrode and to an antenna coil within the antenna coil case.
Figure 2:
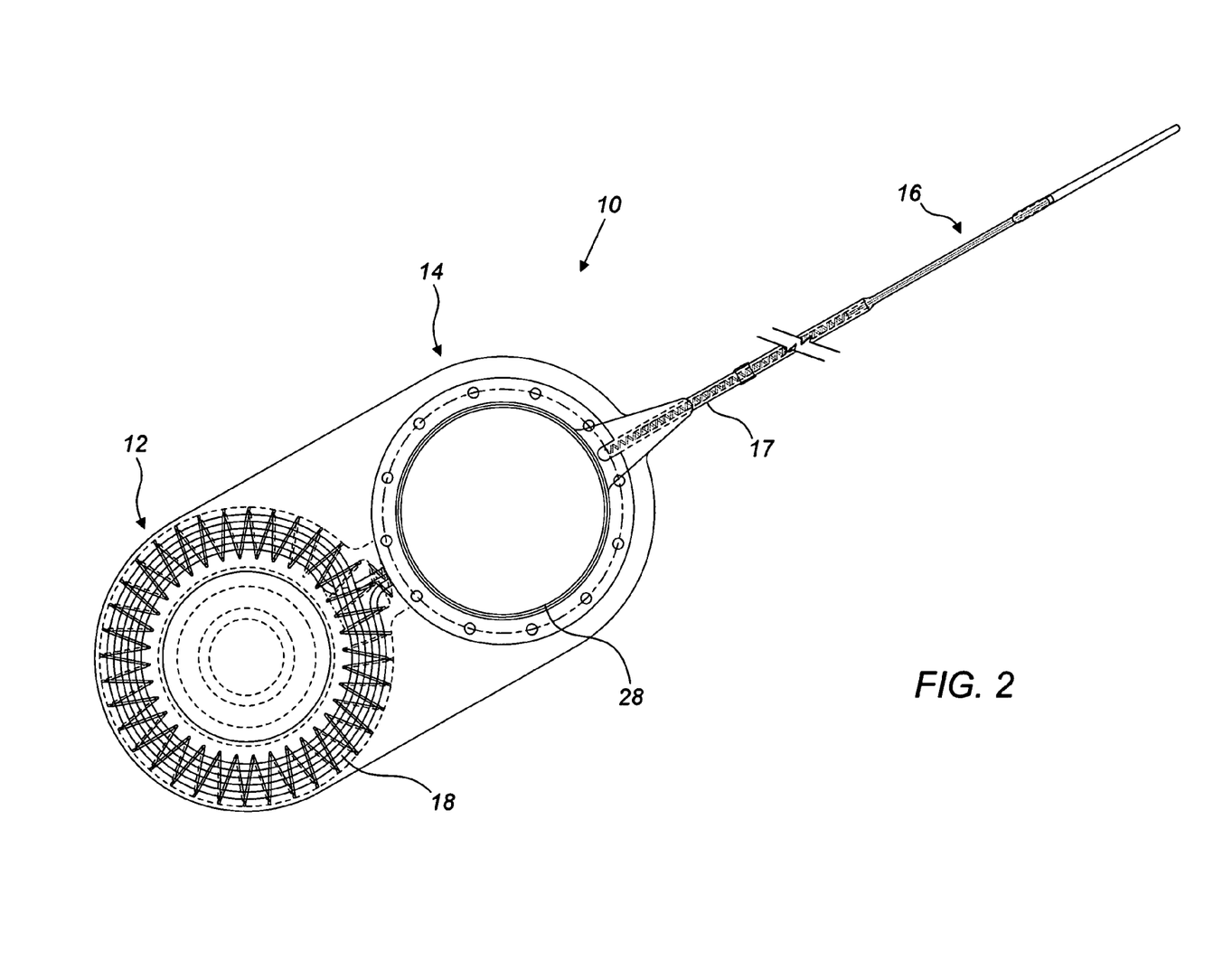
FIG. 2 is bottom view of the system of FIG. 1.
Figure 3:
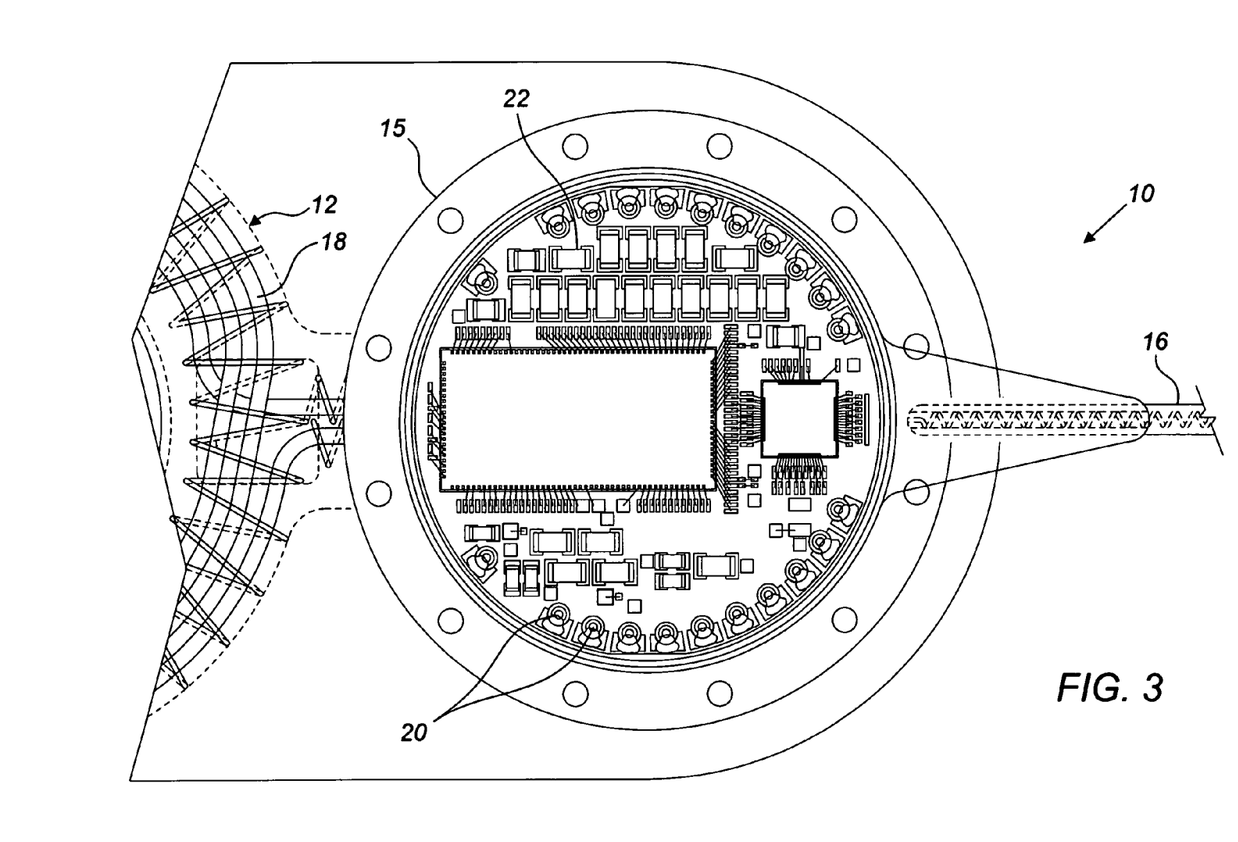
FIG. 3 is an enlarged bottom view of a portion of the coil case and the housing of FIG. 1 with the bottom cover of the feedthrough case removed to show the stimulation circuitry and the feedthrough pins connected to the stimulation circuitry.

FIGS. 1-3 depict an exemplary cochlear implant 10 to which the present invention may be applied, comprising an antenna coil case 12, a housing 14, and a cochlear electrode 16. The coil case 12 houses an antenna 18 electrically connected to upper end portions of metal feedthrough pins 20 supported by and extending through glass insulating seals 24 between top and bottom compartments 11 and 13 of a metal feedthrough case 15 within the housing 14. The feedthrough case 15 contains cochlea stimulation circuitry 22 supported within the bottom compartment 13 and electrically connected to lower portions of the feedthrough pins 20 as diagrammatically depicted in FIG. 1. The cochlear electrode 16 is also connected to the stimulation circuitry 22 via a lead 17 connected to upper end portions of the feedthrough pins 20 within the top compartment 11 as depicted in FIGS. 1 and 3.

Figure 8:
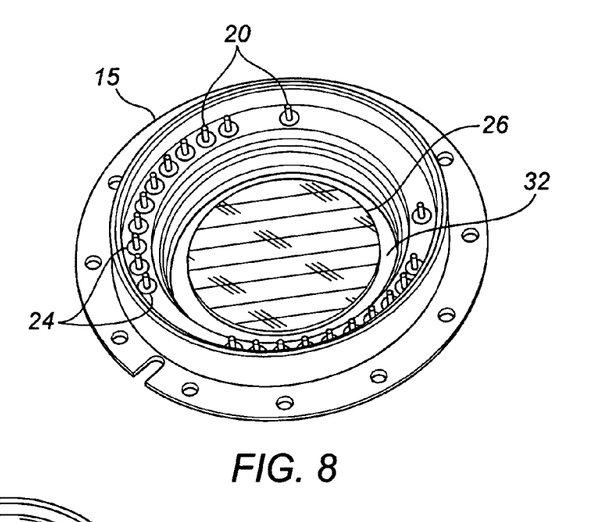
FIG. 8 is a bottom perspective view of the metal feedthrough case without the stimulation circuitry in place and with the moisture absorbing material secured to the feedthrough case.

As illustrated in FIGS. 1 and 8, glass seals 24 surround and insulate the feedthrough pins 20 as they extend between the top and bottom compartments 11 and 13 of the feedthrough case 15. The glass seals 24 are subject to cracking around the feedthrough pins 20 when subjected to excessive forces during assembly, testing, or use. Such cracks have been identified as leak paths for moisture into the bottom compartment 13 of the feedthrough case 15 resulting in damage to the stimulation circuitry 22 housed within the bottom compartment.

Figures 4, 5, 6:
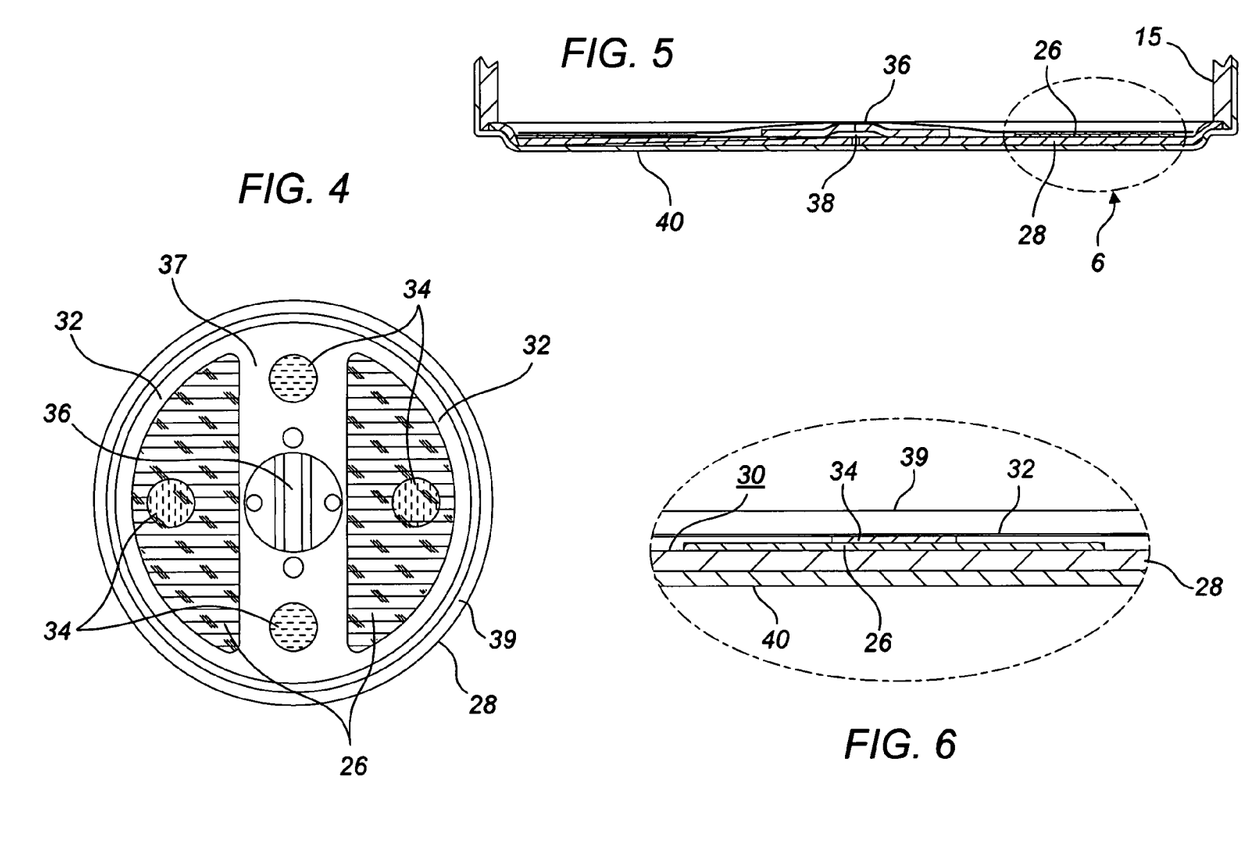
FIG. 4 is an enlarged top view of the bottom cover showing the moisture absorbing material in a kidney shaped configuration secured to the bottom cover under a protective film and laterally spaced on opposite sides of a shield for a vent hole in the bottom cover.
FIG. 5 is an enlarged portion of the cross-sectional view of FIG. 1 within the region 5 showing the metal bottom cover supporting the moisture absorbing material and welded to the feedthrough case to form the bottom compartment housing the stimulation circuitry.
FIG. 6 is an enlarged portion of the cross-sectional view of FIG. 5 within the region 6 showing the moisture absorbing material secured to the bottom cover under a protective film secured to the moisture absorbing material by an adhesive.

As shown in FIG. 4, to prevent moisture released from the stimulation circuitry 22 and moisture leaking into the bottom compartment 13 as through the leak paths in cracked seals 24 from damaging the stimulation circuitry, a quantity of a moisture absorbing material, or getter, 26 comprising calcium oxide is secured in the bottom compartment 13 as by attachment to a metal bottom cover 28 secured and sealed to the feedthrough case 15 to close the bottom compartment. The moisture absorbing material 26 is cured according to the assembly procedures of the present invention as will be described hereafter.

Preferably, the moisture absorbing material is HiCap 2000, a high capacity moisture getter comprising a CaO desiccant, a solvent, and a thermoplastic. HiCap 2000 is available from Cookson Electronics, Alpharetta, Ga., USA. As supplied, HiCap 2000 is a pale blue paste available in standard 3 cc, 5 cc, 10 cc, and 30 cc syringe sizes for manual or automated dispensing. Calcium oxide reacts with water to form calcium hydroxide, thus chemically binding the water. The water will stay chemically bound up to a temperature of 580° C., much higher than the subsequent manufacturing, testing, sterilization, and use temperatures encountered by the device following addition of the getter material.

Through extensive experimentation and testing, applicant has verified that at leak rates of less than $1 \times 10^{-5}$ atm cc/s, the moisture absorbing material 26 is able to absorb moisture within the bottom compartment 13 of the feedthrough case 15 and to maintain the moisture level within product specifications. Conversely, at leak rates higher than $1 \times 10^{-5}$ atm cc/s, the moisture absorbing material 26 is subject to rapid saturation, having a limited useful life. To insure that the moisture absorbing material 26 is not subjected to leak rates higher than $1 \times 10^{-5}$ atm cc/s, the feedthrough pins 20 and the glass seals 24 are enclosed with a protective biocompatible material such as silicone rubber 27. Prior to attaching a top cover 29 to the feedthrough case 13, the silicone 27 may be injected into the top compartment 11 to enclose in silicone the upper ends of the feedthrough pins 20 and the glass seals 24. Alternatively, such silicone enclosing of the feedthrough pins and glass seals may be accomplished during a conventional silicone overmolding of the outer surface of the feedthrough case 15 or entire housing 14 wherein the silicone 27 is injected around the lead 17 and into the top compartment 11 with the top cover 29 enclosing the top compartment 11 secured to the feedthrough case as depicted in FIG. 1. The silicone 27 is impervious to viscous flow of fluid and will not allow fluid to leak into the case 15 at rates of $1 \times 10^{-5}$ atm cc/s or more. However, silicone is permeable to moisture and will allow the passage of moisture at leak rates up to $1 \times 10^{-7}$ atm cc/s. Thus, the silicone 27 functions to slow the leaking process through any silicone enclosed cracks in the glass insulation 24 and around the metal feedthrough pins 20. Therefore, any moisture leaking into the bottom compartment 13 of the feedthrough case 15 housing the stimulation circuitry 22 will have a maximum leak rate of about $1 \times 10^{-7}$ atm cc/s, well within the previously described linear range of leak rate to useful device life. Further, applicant has determined that when used in sufficient quantity and configuration, at leak rates of up to $1 \times 10^{-7}$ atm cc/s, the moisture absorbing material 26 is capable of maintaining moisture levels within the housing 14 within product specifications for over 60 years. In that regard, applicant has determined that the weight of the moisture absorbing material 26 secured on the bottom cover 28 of the housing after curing should be at least about 30 mg and preferably between about 30 mg and about 50 mg, with an exposed surface area between about 0.15 in.$^2$ and about 0.38 in.$^2$ (with 0.25 in.$^2$ being preferred), and a thickness of between about 0.002 inches and about 0.020 inches, preferably between about 0.002 inches and about 0.010 inches, and most preferably about 0.005 inches.

Figure 7:
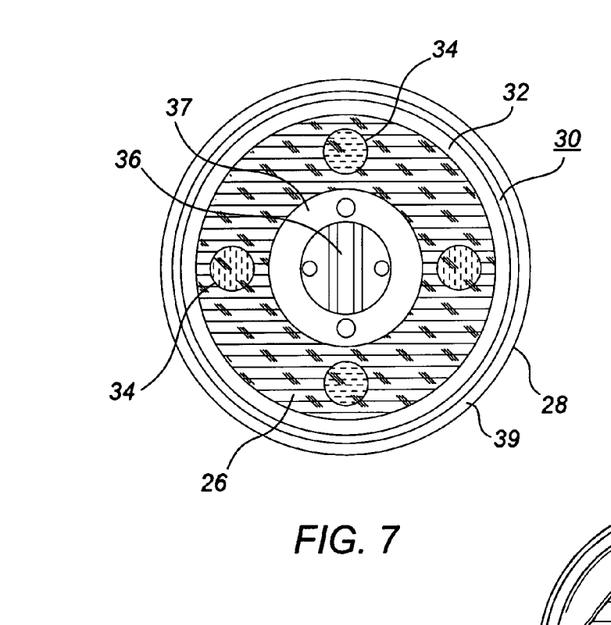
FIG. 7 is a top view of the bottom cover showing the moisture absorbing material in a flat ring configuration secured to the bottom cover under the protective film and surrounding and laterally spaced from a shield for a vent hole in the bottom cover.
Figure 9:
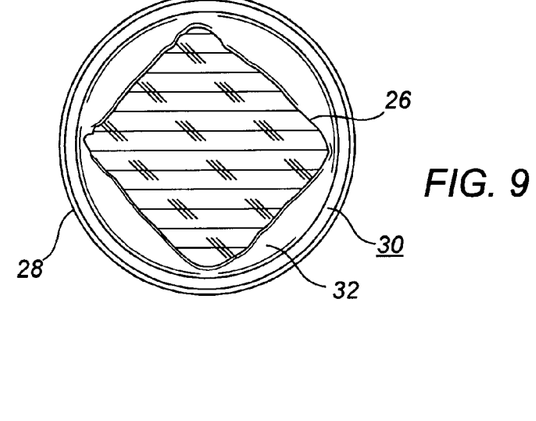
FIG. 9 is a top view of a vent-free bottom cover with the protective film or disk over and secured to the top surface of the bottom cover with a flat layer of moisture absorbing material in the shape of a rectangle secured on top of the film or disk.

Specific embodiments of the bottom cover 28 with the moisture absorbing material, or getter, 26 secured relative to the bottom cover 28 of the housing 14 are depicted in FIGS. 4, 7, and 9.

As shown in FIGS. 4-6, the bottom cover 28 contains a vent hole 38, which is used to vent gases before finally sealing the vent hole to create a hermetically sealed compartment for the stimulation circuitry 22. A shield 36 is provided to protect circuitry 22 from the laser beam used to seal the vent hole. Because of the need to keep the vent hole open for degassing and the need to keep the outer lip 39 of the bottom cover 28 free of getter material to form a good seal of the bottom cover 28 to the feedthrough case 15, the moisture absorbing material 26 is applied manually or by machine in a flat kidney shaped configuration on a top surface 30 of the bottom cover 28, laterally spaced on opposite sides of a vent hole shield 36, leaving a central area 37 adjacent the shield 36 and an upper outer lip 39 of the bottom cover 28 free of moisture absorbing material. As depicted most clearly in FIG. 6, and as will be described later relative to the assembly of the housing, the absorbing material 26 bears directly on and is secured to the top surface 30 of the bottom cover 28 under a protective insulating film or disk 32 that, in turn, is secured to the top of the absorbing material 26 preferably by a silicone adhesive 34, shown as separate circles of adhesive in FIG. 4. Although moisture will penetrate silicone, these discrete regions of adhesive are preferred instead of a continuous layer to adhere the insulating film 32 to the getter to maximize exposure of the getter for absorbing moisture. As previously described, the outer surface of the housing 14 preferably is coated with a protective biocompatible material 40 such as a silicone rubber coating.

As shown in FIG. 7, the moisture absorbing material 26 may be applied in a flat ring configuration secured to the top surface 30 of the bottom cover 28 under the protective film 32 surrounding and spaced from the vent hole shield 36.

FIG. 8 is a bottom perspective view of the metal feedthrough case 15 into which the stimulation circuitry 22 will be placed and to which the bottom cover 28 will be attached. Moisture absorbing material, or getter, 26 is secured to the feedthrough case, either directly or on top of the insulating film 32. When the insulating film is between the getter and the feedthrough case, it preferably comprises polyimide tape having adhesive on one side to facilitate attachment to the feedthrough case. However, when the insulating film is on top of the getter, only discrete regions of adhesive are used to maximize the surface of the getter available to absorb moisture.

FIG. 9 is a top view of a bottom cover assembly without a vent hole. The film 32 of insulation or protective material may be self-adhesive or secured by separate adhesive directly to the top surface 30 of the bottom cover 28, and electrically insulates the circuitry 22 from the metal bottom cover 28. A flat layer of moisture absorbing material 26 is then applied to the top of the film 32 in any shape, with a rectangle shown as an example, and secured to the film either by an adhesive or during the curing of the moisture absorbing material as will be described. Alternatively, the moisture absorbing material 26 may be applied directly to the bottom cover, and film 32 applied over the moisture absorbing material.

The method for assembling a cochlear implant having an extended useful life according to the present invention basically comprises: providing an implantable housing 14 comprising a metal feedthrough case 15 having metal top and bottom covers 29 and 28 closing top and bottom compartments 11 and 13 within the feedthrough case with feedthrough pins 20 extending through insulating seals 24 between the top and bottom compartments; placing cochlea stimulation circuitry 22 within the bottom compartment 13 of the feedthrough case 15; connecting the stimulation circuitry 22 to the feedthrough pins 20; enclosing upper portions of the feedthrough pins 20 and the seals 24 with the silicone 27; securing within the bottom compartment 13 of the feedthrough case 15 at least about 30 mg of cured moisture absorbing material 26 comprising calcium oxide; and sealing the feedthrough case 15 with the bottom and top covers 28 and 29 to form the sealed housing 14.

The providing of the implantable metal feedthrough case 15 housing the circuitry 22 and including feedthrough pins 20 comprises providing the metal feedthrough case 15, providing the circuitry 22 within the case, and connecting the feedthrough pins 20 to the circuitry 22 within the case. The securing of the moisture absorbing material 26 within the housing 14 preferably comprises introducing between about 60 mg and about 100 mg of an uncured moisture absorbing material 26 containing a calcium oxide desiccant, a solvent, and a thermoplastic onto the bottom cover 28 or the feedthrough case 15 so that it has an exposed surface area of between about 0.15 in.$^2$ and about 0.38 in.$^2$, with 0.25 in.$^2$ being preferred, and a thickness of between about 0.002 inches and about 0.010 inches. The moisture absorbing material 26 may be applied manually or using automated equipment. As described earlier, a film 32 of protective or insulating material may be secured to a top surface 30 of the bottom cover 28 or the metal feedthrough case 15 before application of the moisture absorbing material 26. Further, the moisture absorbing material 26 may be applied to and secured to a top surface of the protective film or the film 32 may be applied and secured to a top of the moisture absorbing material 26 after its application and securing to the bottom cover 28 or the feedthrough case 15. Then, the assembly is cured to evaporate the solvent and to melt the thermoplastic of the moisture absorbing material leaving the moisture absorbing material in a solid state with the thermoplastic bonded directly to the housing 14 or to the top of the protective film 32, depending upon the relative location of the film to the layer of moisture absorbing material.

The curing of the moisture absorbing material 26 preferably is in an oven at about 160° C. for at least 30 minutes and preferably for about one to two hours. After curing, the weight of the cured material 26 is between about 30 mg and about 50 mg.

The method of assembly further comprises laser welding the bottom cover 28 to the metal feedthrough case 15. Thereafter, the assembly is vacuum baked to remove any moisture, and the vent hole 38 is sealed by laser welding.

As previously described, the above described method of assembly provides a cochlear implant having an extended life at moisture leak rates up to about $1 \times 10^{-7}$ atm cc/s where the resulting cochlear implants have been shown to have an extended useful life of 60 years or more.

While in the foregoing, preferred embodiments of the present invention and a preferred mode of assembly thereof have been described and illustrated, changes and modifications may be made without departing from the spirit of the present invention. Accordingly the present invention is to be limited in scope only by the following claims.

The invention claimed is:

1. In a cochlear stimulator system, a cochlear implant comprising:
   an implantable sealed housing comprising a metal feedthrough case having separate sealed top and bottom compartments and metal feedthrough pins extending between the top and bottom compartments and having upper and lower end portions respectively within the top and bottom compartments,
   cochlea stimulation circuitry housed with the bottom compartment and electrically connected to lower end portions of the feedthrough pins, upper end portions of the feedthrough pins being electrically connected to a lead from a cochlear electrode to complete a connection between the stimulation circuitry and the cochlear electrode,
   silicone enclosing upper end portions of the feedthrough pins configured to limit any moisture leaking around the feedthrough pins from the top compartment to the bottom compartment housing the stimulation circuitry to leak rates less than about $1\times10^{-7}$ atm cc/s, and
   a moisture absorbing material secured within the bottom compartment of the feedthrough case and comprising calcium oxide sufficient in quantity to absorb any moisture released by the stimulation circuitry and any moisture leaking into the bottom compartment of the feedthrough case at the leak rates less than about $1\times10^{-7}$ atm cc/s and to extend the useful life of the implant.

2. The implant of claim 1 wherein the moisture absorbing material comprises cured HiCap 2000.

3. The implant of claim 1 wherein the metal feedthrough pins are insulated by seals enclosed in silicone that are configured to form moisture leak paths having moisture leak rates less than about $1\times10^{-7}$ atm cc/s and wherein the quantity of moisture absorbing material secured within the sealed housing is configured to extend the useful operating life of the implant to 60 years or more.

4. The implant of claim 3 wherein the outer surface of the sealed housing is covered with silicone sufficient to limit any moisture leaking into the bottom compartment of the housing to leak rates less than $1\times10^{-7}$ atm cc/s.

5. The implant of claim 3 wherein the weight of the moisture absorbing material as cured is at least about 30 mg.

6. The implant of claim 5 wherein the weight of the moisture absorbing material as cured is less than about 50 mg.

7. The implant of claim 5 wherein the moisture absorbing material has an exposed surface area of at least 0.15 in.$^2$.

8. The implant of claim 5 wherein the moisture absorbing material has an exposed surface area of about 0.25 in.$^2$.

9. The implant of claim 5 wherein the moisture absorbing material has a thickness of between about 0.002 inches and about 0.010 inches.

10. The implant of claim 5 wherein the moisture absorbing material is secured to a metal bottom cover enclosing the bottom compartment within the feedthrough case.

11. The implant of claim 10 wherein the bottom cover includes a vent hole free of the moisture absorbing material that is sealed after a curing of the moisture absorbing material.

12. The implant of claim 10 wherein the bottom cover includes an outer border free of the moisture absorbing material.

13. The implant of claim 5 wherein the moisture absorbing material is secured to the feedthrough case.

14. The implant of claim 5 wherein the moisture absorbing material is secured within and directly to the housing, and a film of insulating material is secured to a top of the moisture absorbing material.

15. The implant of claim 5 wherein a film of insulating material is secured within and directly to the housing, and the moisture absorbing material is secured to a top of the film.

16. A method of assembling the cochlear implant of claim 1 characterized by an extended useful operating life of about 60 or more years, comprising:
   providing an implantable sealed housing characterized by a moisture leak rate of less than about $1\times10^{-7}$ atm cc/s and comprising a metal feedthrough case having a metal bottom cover and feedthrough pins for connecting an electrical lead from a cochlear electrode to cochlea simulation circuitry within the feedthrough case;
   placing cochlear stimulation circuitry within the feedthrough case and connecting the circuitry to the feedthrough pins;
   enclosing the feedthrough pins in silicone;
   securing within the housing at least 30 mg of a cured moisture absorbing material comprising calcium oxide, and
   sealing the feedthrough case with the bottom cover.

17. The method of claim 16 wherein the securing comprises applying the moisture absorbing material so that it has an exposed surface area of between about 0.15 in.$^2$ and 0.38 in.$^2$.

18. The method of claim 16 wherein the securing comprises applying the moisture absorbing material so that it has an exposed surface area of about 0.25 in.$^2$.

19. The method of claim 16 wherein the securing comprises applying the moisture absorbing material so that it has a thickness of between about 0.002 inches and about 0.010 inches.

20. The method of claim 16 wherein the securing comprises:
   applying a moisture absorbing material containing a desiccant material and a solvent; and
   curing the moisture absorbing material to evaporate the solvent.

21. The method of claim 20 wherein the sealing comprises laser welding the bottom cover to the feedthrough case.

22. The method of claim 16 wherein the securing comprises:
   applying a moisture absorbing material containing a desiccant, a solvent, and a thermoplastic; and
   curing the moisture absorbing material to evaporate the solvent, melt the thermoplastic, and bond the thermoplastic to the housing.

23. The method of claim 22 wherein the curing is in a oven at about 160° C. for at least 30 minutes.

24. The method of claim 22 wherein the curing is for one to two hours.

25. The method of claim 22 wherein the sealing comprises laser welding the bottom cover to the feedthrough case.

26. The method of claim 25 further including sealing a vent hole in the feedthrough case.

27. The method of claim 16 wherein the securing comprises applying the moisture absorbing material to the bottom cover.

28. The method of claim 16 wherein the securing comprises applying the moisture absorbing material to the feedthrough case.

29. The method of claim 16 wherein the securing comprises applying the moisture absorbing material directly to the housing, and further comprises securing a film of insulating material over and to the moisture absorbing material.

30. The method of claim 16 further comprising:

securing a film of insulating material to the housing; and applying the moisture absorbing material to the film.

* * * * *